(12) United States Patent
Mathieu et al.

(10) Patent No.: US 7,304,191 B2
(45) Date of Patent: Dec. 4, 2007

(54) PROCESS FOR THE SYNTHESIS OF FLUOROORGANIC COMPOUNDS

(75) Inventors: Véronique Mathieu, Wavre (BE); Francine Janssens, Vilvoorde (BE); James Franklin, Brussels (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 10/343,886

(22) PCT Filed: Aug. 6, 2001

(86) PCT No.: PCT/EP01/09081

§ 371 (c)(1),
(2), (4) Date: Feb. 5, 2003

(87) PCT Pub. No.: WO02/12160

PCT Pub. Date: Feb. 14, 2002

(65) Prior Publication Data

US 2004/0024243 A1 Feb. 5, 2004

(30) Foreign Application Priority Data

Jul. 8, 2000 (FR) .................................. 00 10413

(51) Int. Cl.
*C07C 17/00* (2006.01)
*C07C 21/18* (2006.01)
*C07C 53/21* (2006.01)
*C07C 69/63* (2006.01)

(52) U.S. Cl. ................ 570/155; 570/135; 560/227; 562/605

(58) Field of Classification Search ............... 560/226, 560/172, 184, 219; 562/602, 604, 605, 598, 562/553
See application file for complete search history.

(56) References Cited

U.S. PATENT DOCUMENTS 5,124,476 A * 6/1992 Gassen et al. .............. 560/213

FOREIGN PATENT DOCUMENTS

| BE | 786464 | 11/1972 |
|---|---|---|
| BE | 817678 | 3/1977 |
| GB | 590015 | 7/1947 |
| GB | 1466287 | 3/1977 |
| JP | 60158134 | * 8/1985 |
| JP | 60158136 | * 8/1985 |
| JP | 60158137 | * 8/1985 |
| JP | 2001172223 | * 6/2001 |

OTHER PUBLICATIONS

Boguslavskaya, L. S.; Zhurnal Organicheskoi Khimii (1987), 23(6), 1173-7 (Abstract).*
Nishitani et al., Journal of Antibiotics (1988), 41(3), 332-42 (Nishitani), See Chemical Abstracts online citation.*
Chemical ABstract online citation of US 5124476 [retrieved on Aug. 2, 2006] Columbus OH, USA.*
Zhurnal Organicheskoi Khimii (1980), 16(8), 1640-5.*
039804, 1970, Japan.
L.S. Boguslavskaya et al., "alpha-Fluoroacrylates: synthesis, properties and use," Russian Chemical Reviews 59 (9), pp. 906-917, 1990.
XP 002165720—L.S. Boguslavskaya et al., "Oxydative Nucleophilic Fluorination Of C-Br Bonds New Preparative Applications," Journal of Fluorine Chemistry, vol. 54, No. 1-3, Sep. 1991.
K.R. Gassen et al., "Synthese Von alpha-Fluoracrylsaure und Derivaten", Journal of Fluorine Chemistry, vol. 55, No. 2, pp. 149-162, Dec. 15, 1991.
XP 001036784—B.L. Dyatkin et al., "alpha-Fluoro-beta-Haloacrylic Acids", Bulletin of the Academy of the USSR, Div. Chem. Sci. vol. 23, pp. 1581-1583, 1974.
XP 002186066—S. Eddarir et al., "Synthesis of Fluorinated Enynes and Dienes via 1-Bromo 2-Fluoro Alkenes", Tetrahedron Letters, vol. 32, No. 1, pp. 69-72, 1991.
XP 002186067—Y. Takeuchi et al., "Synthetic studies for novel structure of alpha-nitrogenously functionalized alpha-fluorocarbooxylic acids. Part III. Some reactions of alpha-bromo-alpha-fluorocarboxylic acids and their ethyl esters with sodium azide", Journal of Fluorine Chemistry, vol. 68, pp. 149-154, 1994.
C. Botteghi et al., "A new preparative route to alpha-fluoroacrylic acid", Journal of Fluorine Chemistry, vol. 107, pp. 113-116, 2001.

* cited by examiner

*Primary Examiner*—Karl Puttlitz
(74) *Attorney, Agent, or Firm*—Connolly Bove Lodge & Hutz LLP

(57) ABSTRACT

The present invention relates to a fluorination method for the synthesis of halofluoroorganic compounds which can be used, inter alia, as precursors in the synthesis of 2,3-unsaturated fluoroorganic carbonyl compounds comprising a fluorine substituent in the 2 position.

8 Claims, No Drawings

PROCESS FOR THE SYNTHESIS OF FLUOROORGANIC COMPOUNDS

The present invention relates to a fluorination method for the synthesis of halofluoroorganic compounds which can be used, inter alia, as precursors in the synthesis of fluoroorganic compounds. It also relates to certain halofluoroorganic compounds, to a process for the synthesis of fluoroorganic compounds and to the use of the said fluoroorganic compounds as a synthetic intermediate, in particular as a (co) monomer.

2,3-Unsaturated organic carbonyl compounds comprising a fluorine substituent in the 2 position, such as, for example, 2-fluoropropenoic acid derivatives, can be used as an intermediate in the synthesis of organic compounds, particularly in the manufacture of fluorooligomers or fluoropolymers which can be used, for example, in the manufacture of synthetic glass of high mechanical strength or in the manufacture of optical fibres.

A review article (Boguslavskaja et al., Russian Chemical Reviews, 59 (9), 1990, p. 906-917) describes methods for the synthesis of 2-fluoropropenoic acid derivatives. The various methods described in this article however exhibit numerous disadvantages, such as, inter alia, an unsatisfactory overall yield of 2-fluoropropenoic acid derivatives, a high number of stages, difficult accessibility to the precursors of the 2-fluoropropenoic acid derivatives or alternatively use of reactants which are difficult to access and expensive, such as interhalogen compounds.

The invention is targeted at providing an efficient process for the synthesis of 2,3-unsaturated organic carbonyl compounds comprising a fluorine substituent in the 2 position and in particular of 2-fluoro-2-alkenoic acid derivatives which does not exhibit the abovementioned disadvantages. The invention is also targeted at providing efficient precursors of organic carbonyl compounds, the said precursors being able to be obtained economically from readily accessible products.

The invention consequently relates to a fluorination method for the synthesis of a halofluoroorganic compound of general formula HR'R"C—CXF—(C=O)—Y (I) in which X denotes a halogen atom and Y, R' and R" denote substituents, according to which fluorination method hydrogen fluoride is reacted with an organic compound which corresponds to a general formula chosen from R'R"C=CX—(C=O)—Y (II) and R'R"HC—CX1X2—(C=O)—Y (III) in which X1 and X2 denote halogen atoms.

It has been found that the halofluoroorganic compounds of general formula (I) in which X denotes a halogen atom are efficient precursors of 23-unsaturated organic carbonyl compounds comprising a fluorine substituent in the 2 position. The fluorination method according to the invention makes possible access to the said halofluoroorganic compounds with a high yield and a high selectivity from economical and readily accessible starting materials and reactants.

For the purposes of the present invention, the term 'halogen atom' and the term 'halo' are intended to denote in particular chlorine, bromine and iodine. Chlorine and bromine are preferred among these halogens. Chlorine is very particularly preferred.

For the purposes of the present invention, Y denotes a substituent. It is clearly understood that, between two compounds with different general formulae, Y is not necessarily identical, as it is optionally possible for Y to undergo a modification during a chemical reaction in the context of the invention. Y can be chosen, for example, from H, alkyl, haloalkyl, aryl, OH, OR, $NH_2$, NHR, $NR_2$ and SR in which R denotes a substituent other than hydrogen which, may be selected, for example from the group consisting of alkyl, alkenyl and aryl groups. The organic compound comprising Y is then chosen from aldehydes, ketones, carboxylic acids, esters, amides and thioesters. In the context of the invention, the organic compound comprising Y is often chosen from carboxylic acids, esters, amides and thioesters. It is preferably chosen from carboxylic acids and esters.

For the purposes of the present invention, R' and R" are intended to denote substituents in the various compounds. R' and R" can be identical or different. In an alternative form, the R' and R" substituents are chosen from hydrogen and fluorine, chlorine, bromine and iodine atoms. These substituents are preferably chosen from hydrogen, fluorine and chlorine. In another alternative form, the R' and R" substituents are chosen from hydrogen and hydrocarbonaceous substituents, such as, for example, alkyl, alkenyl or aryl groups. Compounds in which R' and R" denote hydrogen atoms are preferred for the purposes of the present invention.

In a first preferred alternative form of the fluorination method according to the invention, the organic compound is a carboxylic acid which can additionally carry substituents as described above. Particularly preferred examples of such acids are 2,2-dihalopropionic acids and 2-halopropenoic acids.

2,2-Dichloropropionic acid is highly suitable as 2,2-dihalopropionic acid. This is because 2,2-dichloropropionic acid has been marketed as a herbicide. It is consequently readily accessible in industrial amounts and easy synthetic methods are available, such as, for example, the chlorination of propionic acid disclosed, inter alia, in JP-A-45/039804.

2-Chloropropenoic acid is highly suitable as 2-halopropenoic acid. It can be easily obtained, for example from acrylic acid according to the methods disclosed in BE 786 464 and BE 817 678.

In a second preferred alternative form, the fluorination method according to the invention applies to the production of esters of 2-halo-2-fluorocarboxylic acids by reaction of hydrogen fluoride with esters of carboxylic acids as mentioned above.

In this case, the carboxyl group of the carboxylic acid is generally esterified with a radical comprising at least 1, more frequently at least 2, carbon atoms. The carboxyl group of the carboxylic acid is generally esterified with a radical comprising at most 20, more frequently at most 12, carbon atoms. The radical often comprises at least one substituent chosen from chlorine and fluorine. In an alternative form, the radical is an alkyl chain comprising at least one trichloromethyl group. In this alternative form, the radical is preferably a 2,2,2-trichloroethyl radical. In another alternative form, the radical is an alkyl chain comprising at least one trifluoromethyl group. In this alternative form, the radical is preferably chosen from the 2,2,2-trifluoroethyl radical and the 1,1,1,3,3,3-hexafluoro-2-propyl radical. The esters can be obtained by conventional methods, for example by reaction of the carboxylic acid or of an acid halide derived from this carboxylic acid with the alcohol corresponding to the desired radical.

It is clearly understood that the esters of 2-halo-2-fluorocarboxylic acids can also be obtained by subsequent esterification of 2-halo-2-fluorocarboxylic acids obtained according to the fluorination method according to the invention.

In the fluorination method according to the invention, the reaction between the organic compound and the hydrogen fluoride can be carried out in the presence of a fluorination catalyst.

Mention may be made, among the catalysts which can be used, of derivatives of the metals chosen from the metals from Groups IIIa, IVa and b, Va and b, VIb of the Periodic Table of the Elements (IUPAC 1970) and their mixtures. Titanium, tantalum, molybdenum, boron, tin and antimony derivatives are more especially selected. Preferably, titanium or tin derivatives are employed. Tin derivatives are particularly well suited. Mention may be made, as derivatives of the metals, of salts and more particularly halides. The choice is preferably made from chlorides, fluorides and chlorofluorides. Catalysts which are particularly preferred in the fluorination method according to the invention are titanium and tin chlorides, fluorides and chlorofluorides and their mixtures.

Titanium tetrachloride and tin tetrachloride are particularly well suited. Tin tetrachloride is preferred.

The reaction can also be carried out in the absence of catalyst. This alternative form is particularly well suited when an organic compound of general formula (II) described above is reacted with hydrogen fluoride.

The reaction is preferably carried out in the liquid phase.

The reaction can be carried out continuously or batchwise. A batchwise reaction is well suited.

The reaction can be carried out in the absence of solvent. It is also possible to use a solvent in which the organic compound is soluble. Such solvents are, for example, polar solvents, such as nitrites, amides and esters.

In the reaction, the hydrogen fluoride and the organic compound are generally employed in an HF/organic compound molar ratio of at least 1. The molar ratio is preferably at least 3. The HF/organic compound molar ratio is generally at most 20. The molar ratio is preferably at most 12.

If a catalyst is used in the reaction, the catalyst and the organic compound are generally employed in a catalyst/organic compound molar ratio of at least 0.01. This molar ratio is preferably at least 0.05. The catalyst/organic compound molar ratio is generally at most 1. This molar ratio is preferably at most 0.5.

The temperature of the reaction is generally at least 50° C. The temperature is more frequently at least 80° C. The temperature is preferably at least 90° C. The temperature of the reaction is generally at most 200° C. The temperature is more frequently at most 150° C. The temperature is preferably at most 130° C.

The pressure of the reaction is generally at least 1 bar. The pressure is generally at most 100 bar, preferably at most 50 bar.

In a particular embodiment, it might be advantageous to limit the conversion of the organic compound in order to optimise the yield of halofluoroorganic compound. In this embodiment, the conversion of the organic compound is generally kept at 80% or less, preferably about 70% or less.

The halofluoroorganic compound can be recovered from the reaction medium by separation techniques known as such, such as, for example, in particular a distillation. Unconverted organic compound may be suitably recycled to the reaction with hydrogen fluoride.

The halofluoroorganic compounds resulting from the fluorination reaction can be subjected to subsequent reactions intended to modify the Y substituent, such as, for example, the esterification reaction, mentioned above, of a carboxylic acid.

When Y is OH, the halofluoroorganic compound is a 2-halo-2-fluorocarboxylic acid. The 2-halo-2-fluorocarboxylic acid is preferably a 2-halo-2-fluoropropionic acid. 2-Chloro-2-fluoropropionic acid is more particularly preferred.

When Y is OR, the halofluoroorganic compound is an ester of 2-halo-2-fluorocarboxylic acid. The preferred esters are the esters of the preferred 2-halo-2-fluorocarboxylic acids in which the carboxyl group of the carboxylic acid is esterified with a radical comprising at least one atom chosen from chlorine and fluorine and more particularly the radicals mentioned above.

The invention also relates to an organic product composed essentially of halofluoroorganic compounds as described above. The invention also relates in particular to 2-halo-2-fluorocarboxylic acids and esters of 2-halo-2-fluorocarboxylic acids. The invention also relates to 2-chloro-2-fluoropropionic acid.

The halofluoroorganic compounds which can be obtained according to the fluorination method according to the invention are intermediates which can be used in organic synthesis. They are well suited to the synthesis of fluoroorganic compounds of general formula R'R"C=CF—(C=O)—Y (IV). They are particularly well suited to the synthesis of 2-fluoro-2-alkenoic acids and esters of 2-fluoro-2-alkenoic acids.

The invention consequently also relates to a process for the synthesis of a fluoroorganic compound of general formula R'R"C=CF—(C=O)—Y (IV) comprising a stage (a) in which a precursor comprising a halofluoroorganic compound of general formula HR'R"C—CXF—(C=O)—Y (I), in which X denotes a halogen atom, is subjected to a dehydrohalogenation reaction.

In the process according to the invention, the precursor is often composed essentially of a halofluoroorganic compound of general formula HR'R"C—CXF-(C=O)—Y (I) as described above. The precursor is preferably chosen from 2-halo-2-fluorocarboxylic acids and esters of 2-halo-2-fluorocarboxylic acids. In the process according to the invention, the precursor was preferably obtained according to the fluorination method according to the invention. The fluoroorganic compounds resulting from the dehydrohalogenation reaction can be subjected to subsequent reactions intended to modify the Y substituent, such as, for example, the esterification reaction, mentioned above, of a carboxylic acid.

In a particular embodiment, the precursor comprises, in addition to the a halofluoroorganic compound of general formula (I), at least an organic compound selected from the organic compounds of general formulae (II) and (III) described above. Such a precursor may be obtained, for example, by a simple separation of organic constituants from inorganic constituants of the reaction medium obtained by the fluorination method of the invention, for example by extraction or distillation. Organic compound of general formula (III) is generally converted by the dehydrohalogenation reaction into an organic compound of general formula (II). The organic compounds of general formula (II) or (III) which, in this particular embodiment, are contained in the reaction mixture produced by the dehydrohalogenation reaction, may be suitably separated from the fluoroorganic compound of general formula (IV) by separation techniques such as, for example, a distillation or crystallisation. The organic compounds of general formula (II) or (III) can be preferably recycled to a reaction with hydrogen fluoride according to the fluorination method of the invention.

The dehydrohalogenation reaction can be carried out, for example, by reaction with a base, by the thermal route or by reaction in the presence of a dehydrohalogenation catalyst, such as, for example, an organometallic catalyst.

The reaction with a base is preferred. Mention may be made, as bases, of alkali metal hydroxide solutions, amines and alkoxides. Mention may in particular be made of aqueous sodium hydroxide solutions.

The dehydrohalogenation temperature is generally at least 40° C. The temperature is preferably at least 60° C. The dehydrohalogenation temperature is generally at most 200° C. The temperature is preferably at most 150° C.

The concentration of the precursor in the reaction medium is generally at least 5% by weight. The concentration is generally at most 50% by weight.

The pressure at which the dehydrohalogenation is carried out is generally from 1 bar to 20 bar.

The fluoroorganic compound can be recovered by conventional techniques, such as, for example, an extraction. Nitriles, such as, in particular, propionitrile, or ethers, such as, in particular, diethyl ether, are well suited as extraction solvent.

In a preferred alternative form, the process according to the invention comprises
(a) a stage in which an organic compound which corresponds to a general formula chosen from R'R"C=CX—(C=O)—Y (II) and R'R"HC—CX1X2-(C=O)—Y (III) as described above is reacted according to the fluorination method according to the invention to produce a halofluoroorganic compound of general formula HR'R"C—CXF—(C=O)—Y (I);
(b) a stage in which the halofluoroorganic compound is subjected to a dehydrohalogenation;
(c) a stage in which optionally at least one reaction intended to modify the Y substituent is carried out;
(d) a stage in which a fluoroorganic compound of general formula R'R"C=CF—(C=O)—Y (IV) is recovered.

The process according to the invention is particularly well suited to the production of fluoroorganic compounds chosen from 2-fluoropropenoic acid and esters of 2-fluoropropenoic acid.

The invention also relates to the use of the fluoroorganic compound of general formula R'R"C=CF—(C=O)—Y (IV) obtained according to the process according to the invention as monomer or comonomer in a process for the manufacture of a fluoropolymer or fluorooligomer.

The term 'fluorooligomer' is understood to denote an organic body comprising at least 2 and at most 50 monomer units, including at least one monomer unit obtained according to the process according to the invention. The term 'fluoropolymer' is understood to denote an organic body comprising more than 50 monomer units, including at least one monomer unit obtained according to the process according to the invention.

The polymerization reaction can, for example, be a radical polymerization. The molecular mass can be controlled by conventional methods.

The examples given below are intended to illustrate the invention without, however, limiting it.

EXAMPLE 1

Synthesis of 2-chloro-2-fluoropropionic Acid 100 g of 2,2-dichloropropionic acid, 123 g of HF and 33 g of $SnCl_4$ were introduced into a 0.5 l stainless steel autoclave. The reaction mixture was heated at 110° C. for 18 h. The liquid phase collected after cooling the autoclave and degassing was analysed by GC (gas chromatography). The conversion of the 2,2-dichloropropionic acid was 75%. The selectivity for 2-chloro-2-fluoropropionic Acid was 97%.

EXAMPLE 2

Synthesis of 2-chloro-2-fluoropropionic Acid 45 g of 2,2-dichloropropionic acid, 61 g of HF and 17.5 g of $SnCl_4$ were introduced into a 0.5 l stainless steel autoclave. The reaction mixture was heated at 120° C. for 5 h. The liquid phase collected after cooling the autoclave and degassing was analysed by GC. The conversion of 2,2-dichloropropionic acid was 61%. The selectivity for 2-chloro-2-fluoropropionic acid was 70%.

EXAMPLE 3

Synthesis of 2,2,2-trifluoroethyl 2-chloro-2-fluoropropionate

Stage A—Synthesis of 2,2,2-trifluoroethyl 2,2-dichloropropionate: 20 g of 2,2-dichloropropionic acid and 18 g of thionyl chloride were heated at reflux for 5 h. After cooling, the liquid phase was analysed by GC. The degree of conversion of the 2,2-dichloropropionic acid was 78%. 10 g of 2,2-dichloropropionyl chloride obtained and 6 g of 2,2,2-trifluoroethanol were introduced into a round-bottomed flask placed in an ice bath. 6.5 g of triethylamine were added to the reaction mixture over 2 h. After reacting for an additional 2 h, approximately 50 ml of water were added. The aqueous and organic phases were subsequently separated and the organic phase was analysed by GC. The 2,2,2-trifluoroethanol was converted to 77%. The yield of ester, based on the amount of 2,2-dichloropropionic acid employed in the first stage, was 65%.

Stage B—Hydrofluorination of 2,2,2-trifluoroethyl 2,2-dichloropropionate : 28 g of 2,2,2-trifluoroethyl 2,2-dichloropropionate, 30 g of HF and 2.7 g of $SnCl_4$ were introduced into a 0.5 l stainless steel autoclave. The reaction mixture was heated at 100° C. for 24 h. The liquid phase collected after cooling the autoclave and degassing was analysed by GC. The conversion of the ester was 84%. The selectivity for 2,2,2-trifluoroethyl 2-chloro-2-fluoropropionate was 95%.

EXAMPLE 4

Synthesis of 2-fluoroacrylic Acid 31 g of 2-chloro-2-fluoropropionic acid were dissolved in 320 ml of a 2N NaOH solution and heated at 100° C. for 24 h. The medium was subsequently acidified with 140 ml of 2N HCl. The 2-fluoroacrylic acid was extracted with two times 200 ml of diethyl ether. 20 g of 2-fluoroacrylic acid were recovered after evaporation of the ether. The yield of 2-fluoroacrylic acid, based on the amount of 2-chloro-2-fluoropropionic acid employed, was 90%.

EXAMPLE 5

Synthesis of 2,2,2-trifluoroethyl 2-fluoroacrylate 10 g of 2-fluoroacrylic acid and 16 g of thionyl chloride were heated at reflux for 6 h. After cooling, the liquid phase was analysed by GC. The conversion of the 2-fluoroacrylic acid was complete. 10 g of 2-fluoroacryloyl chloride obtained and 13 g of 2,2,2-trifluoroethanol were introduced into a round-bottomed flask placed in an ice bath. 13 g of triethylamine were added portionwise to the reaction mixture. After reacting for an additional 3 h, approximately 30 ml of water were added. The aqueous and organic phases were subsequently separated and the organic phase was analysed by GC. The conversion of the 2,2,2-trifluoroethanol was 77%. The yield of ester, based on the amount of 2-fluoroacrylic acid employed in the first stage, was 70%.

EXAMPLE 6

Synthesis of 1,1,1,3,3,3,-hexafluoro-2-propyl 2-fluoroacrylate 12 g of 2-fluoroacryloyl chloride and 27 g of 1,1,1,3,3,3-hexafluoro-2-propanol were introduced into a round-bottomed flask placed in an ice bath. 16 g of triethylamine were added portionwise to the reaction mixture. After reacting for an additional 3 h, approximately 70 ml of water were added. The aqueous and organic phases were subsequently separated and the organic phase was analysed by GC. The conversion of the 1,1,1,3,3,3-hexafluoroisopropanol was 68%. The yield of ester, based on the amount of 2-fluoroacrylic acid employed in the first stage, was 66%.

EXAMPLE 7

Synthesis of 2,2,2-trichloroethyl 2-fluoroacrylate 12 g of 2-fluoroacryloyl chloride and 26 g of 2,2,2-trichloroethanol were introduced into a round-bottomed flask placed in an ice bath. 17 g of triethylamine were added portionwise to the reaction mixture. After reacting for an additional 3 h, approximately 50 ml of water were added. The aqueous and organic phases were subsequently separated and the organic phase was analysed by GC. The conversion of the 2,2,2-trichloroethanol was 52%. The yield of ester, based on the amount of 2-fluoroacrylic acid employed in the first stage, was 67%.

It is apparent that the fluorination method according to the invention makes possible efficient synthesis of halofluoroorganic synthetic intermediates which are advantageous in particular as precursors of 2,3-unsaturated carbonyl compounds carrying a fluorine substituent in the 2 position. The process according to the invention makes possible efficient access in a way which can be operated industrially to these fluoroorganic compounds, which can be used in particular as monomer or comonomer in the manufacture of fluoropolymers or fluorooligomers.

The invention claimed is:

1. A process for the synthesis of a fluoroorganic compound of general formula (IV),

R'R''C=CF—(C=O)—Y (IV), comprising a stage (a) in which a halofluoroorganic compound of general formula (I),

HR'R''C—CXF—(C=O)—Y (I), in which X denotes a halogen atom and
Y is H, alkyl, haloalkyl, aryl, OH, OR, NH$_2$, NHR, NR$_2$ or SR in which R is alkyl, alkenyl or aryl,
R' is hydrogen, fluorine, chlorine, iodine or hydrocarbonaceous substituents,
R'' is hydrogen, fluorine, chlorine, iodine or hydrocarbonaceous substituents, is subjected to a dehydrohalogenation reaction.

2. A process for the synthesis of a fluoroorganic compound of general formula (IV),

R'R''C=CF—(C=O)—Y (IV), comprising a stage (a) in which a precursor consists essentially of a halofluoroorganic compound of the general formula (I),

HR'R''C—CXF—(C=O)—Y (I), in which X denotes a halogen atom and
Y is H, alkyl, haloalkyl, aryl, OH, OR, NH$_2$, NHR, NR$_2$ or SR in which R is alkyl, alkenyl or aryl,
R' is hydrogen, fluorine, chlorine, iodine or hydrocarbonaceous substituents,
R'' is hydrogen, fluorine, chlorine, iodine or hydrocarbonaceous substituents, is subjected to a dehydrohalogenation reaction.

3. The process according to claim 1, in which the halofluoroorganic compound is selected from the group consisting of 2-halo-2-fluorocarboxylic acids and esters of 2-halo-2-fluorocarboxylic acids.

4. The process according to claim 1, in which the halofluoroorganic compound was obtained according to a synthesis wherein hydrogen fluoride is reacted with an organic compound which corresponds to a general formula (II) or (III),

R'R''C=CX—(C=O)—Y (II)

R'R''HC—CX1X2-(C=O)—Y (III), in which X1 and X2 denote halogen atoms,
X denotes a halogen atom and
Y is H, alkyl, haloalkyl, aryl, OH, OR, NH$_2$, NHR, NR$_2$ or SR in which R is alkyl, alkenyl or aryl,
R' is hydrogen, fluorine, chlorine, bromine, iodine or hydrocarbonaceous substituents, and
R'' is hydrogen, fluorine, chlorine, bromine, iodine or hydrocarbonaceous substituents.

5. The process as claimed in claim 1, wherein R' and R'' are hydrogen.

6. A process for the manufacture of a fluoropolymer or fluorooligomer comprising polymerizing or oligomerizing the monomer of the fluoroorganic compound of general formula (IV)

R'R''C=CF—(C=O)—Y (IV), obtained according to the process according to claim 1.

7. The process as claimed in claim 5, wherein said organic compound comprising Y is OH or OR selected from the group consisting of carboxylic acids and esters.

8. A process for the synthesis of a fluoroorganic compound of general formula (IV),

R'R''C=CF—(C=O)—Y (IV), comprising a stage (a) in which a halofluoroorganic compound of general formula (I),

HR'R''C—CXF—(C=O)—Y (I), in which X denotes a halogen atom and
Y is H, alkyl, haloalkyl, aryl, OH, OR, NH$_2$, NHR, NR$_2$ or SR in which R is alkyl, alkenyl or aryl,
R' is hydrogen, fluorine, chlorine, iodine or hydrocarbonaceous substituents,
R'' is fluorine, chlorine, iodine or hydrocarbonaceous substituents, is subjected to a dehydrohalogenation reaction.

* * * * *